United States Patent [19]

Emmerich nee Giesche

[11] 4,364,135
[45] Dec. 21, 1982

[54] ORTHOPEDIC DEVICE TO PREVENT DISTORTION OF INFANT'S FEET

[76] Inventor: Monika Emmerich nee Giesche, Wildwechsel 4, 3167 Burgdorf-Ehlershausen, Fed. Rep. of Germany

[21] Appl. No.: 211,178

[22] Filed: Nov. 28, 1980

[51] Int. Cl.³ .......................... A61F 5/00; A47G 9/00
[52] U.S. Cl. ........................................ 5/443; 128/80 R
[58] Field of Search ....................... 5/443, 444; 128/80

[56] References Cited

U.S. PATENT DOCUMENTS

| | | | |
|---|---|---|---|
| 3,345,656 | 10/1967 | Steinman | 5/443 |
| 3,505,994 | 4/1970 | Smith | 5/443 |
| 3,511,233 | 5/1970 | Holy | 5/444 |
| 3,604,023 | 9/1971 | Lynch | 5/443 |
| 3,946,451 | 3/1976 | Spann | 5/443 |
| 4,104,746 | 8/1978 | Gertz | 5/443 |

*Primary Examiner*—Alexander Grosz
*Attorney, Agent, or Firm*—Penrose Lucas Albright

[57] ABSTRACT

A toroid or roughly similarly-shaped ankle support which receives and holds an infant's toes, with the infant lying stomach down, spaced a short distance above the surface of the bed. The support is relatively thick where it receives the ankle and is composed of a resilient, soft material to prevent injury. In one embodiment, the support is circular and in the other embodiment, it is rectangular with a portion at the top defined to receive the ankle and tied to the infant's ankle.

4 Claims, 3 Drawing Figures

ORTHOPEDIC DEVICE TO PREVENT DISTORTION OF INFANT'S FEET

BACKGROUND OF THE INVENTION

The invention relates to a device for preventing infants and others from placing their feet in a level position while lying prone, i.e., on their bellies on a support, for example, a bed mattress.

It is known from experience that infants favor the prone position, lying on their stomachs when they are lying down, a position which moreover is considered very favorable by specialized physicians. In this position on their stomachs infants place their feet in the level position whereby the tips of the toes are generally parallel to the supporting surface, for example, to the mattress or similar surfaces and point outward or also inward. This position is assumed instinctively by infants because a position in which the toes are generally vertical to the supporting surface, if not exactly painful, is nevertheless uncomfortable. The level position of the feet with the toes pointing outward or inward is, however, from the orthopedic point of view, so extraordinarily unfavorable that structural deformity of the foot may result, the elimination of which is possible only with great difficulty.

SUMMARY OF THE INVENTION

This is the point of departure for the concept of the invention. The invention has as its object a simple and economical means, whereby the placing of the feet in a level position while the infant or others are in the prone position is avoided with certainty.

This object is achieved with a device of the above-mentioned type whereby the device consists of a support attachable to each ankle of the infant, such support holding the toes pointing somewhat vertically or perpendicularly relative to the supporting surface and at a predetermined distance therefrom.

By means of the invention, the feet of the infant are, so to speak, "jacked up" whereby even in the perpendicular position the tips of the toes are spaced above the supporting surface and the position is entirely comfortable and never painful.

According to a preferred embodiment, the support is constructed as a ring which encloses the corresponding ankle.

It is advantageous for the ring to consist of resiliently elastic material, for example, foam rubber or plastic. The ring is so dimensioned whereby irrespective of the compression thereto resulting from the applied weight, the required space between the toes on one hand and the supporting surface on the other is maintained.

It is also within the ambit of the invention that the support may be in a form other than a ring or annular shape. The only requirement is the "jacking up" of the toes so they point in a generally vertical position in relation to the supporting surface.

Some examples of the construction of the device according to the invention are described, generally more specifically, below and illustrated by means of the drawing. In this drawing, these are shown in a purely schematic manner;

DESCRIPTION OF THE PREFERRED EMBODIMENT

Figure 1:
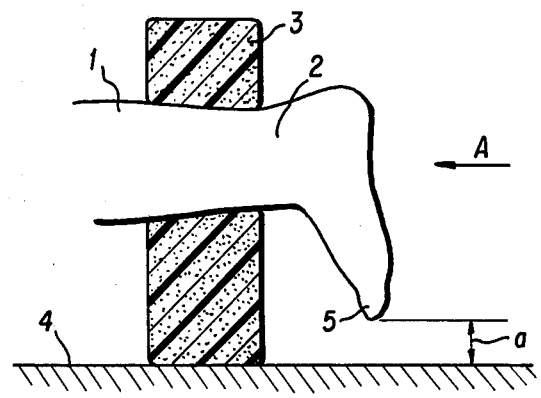
FIG. 1. A partial view of the feet of the infant in the prone position, as well as a vertical section through the device according to the invention.
Figure 2:
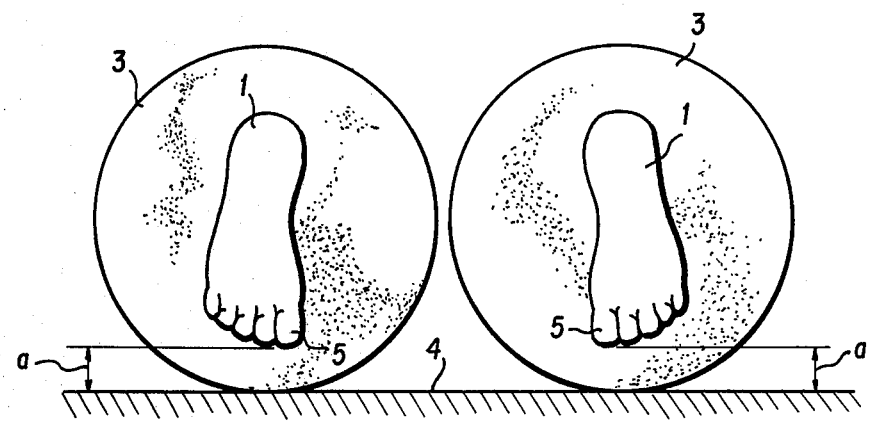
FIG. 2. A view in the direction of the arrow A in FIG. 1.

FIG. 1 of the drawing shows a partial view of the feet 1 with the ankle 2 of the infant in the prone position while the device according to the invention is indicated with reference numeral 3. The device consists thus of a support appliable to each ankle 2 of the infant, which support holds the toes 5 pointed in a somewhat vertical position to the supporting surface 4 with relation to this supporting surface 4 with relation to this supporting surface 4 at a predetermined distance a (FIGS. 1 and 2). In the embodiment represented in FIGS. 1 and 2, the device 3 is constructed as a ring which surrounds the corresponding ankle 2. It is clear that the inside opening of this ring is dimensioned whereby it is possible to place the ring on the ankles 2 of the infant in a comfortable manner.

It is necessary that the ring consists of a resiliently elastic material, for example, foam rubber or foam plastic in order not to produce pressure marks in the area covered by the surrounding structure. In this case the ring is so dimensioned that even if it is compressed as the result of the burden of weight, the distance a is always preserved.

Figure 3:
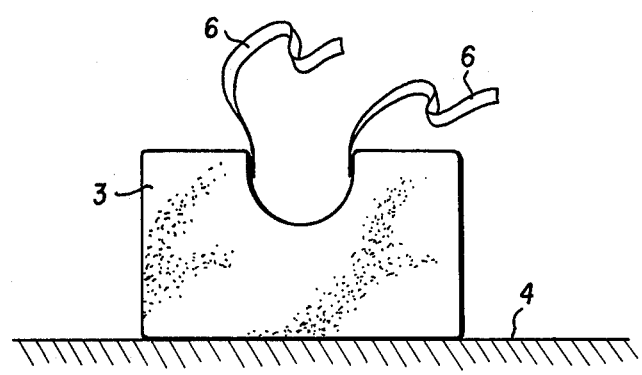
FIG. 3. A view of a further embodiment of the device according to the invention.

FIG. 3 of the drawing shows a somewhat altered form of execution of the device according to the invention. In this case the device has a rectangular shape whereby its connection with the respective ankle 2 is accomplished by means of two strips 6 or something similar.

Before the infant is placed in the bed or something similar, the support is connected in a suitable way with the respective ankle 2. The infant can then also choose a position of the foot while it is in the prone position as this position is shown in FIGS. 1 and 2 and in which injury to the position does not occur.

I claim:

1. An orthopedic device which permits the wearer to retain full range of motion by his ankle when his knee bears against an underlying supporting surface and his feet are pointed naturally downwardly, the device comprising: a body composed of a relatively compressible material and having the configuration of a cylinder which has a greater diameter than its thickness; an opening extending through said thickness of said cylinder, said opening being so dimensioned that the device can be placed over the wearer's foot and worn by him at a location above the foot proximate his ankle in a comfortable manner and cannot be readily dislocated by him when his knee bears against an underlying supporting surface with his leg between the knee and ankle being generally parallel to such supporting surface; the dimension of said body from said opening to said body's periphery being sufficient that said periphery is spaced beyond the wearer's toes when said body is compressed by the wearer's weight thereon between said opening and said periphery proximate the wearer's toes which therefore do not touch the underlying supporting surface.

2. An orthopedic device according to claim 1, wherein said body is composed of a resiliently elastic material.

3. An orthopedic device according to claim 2, wherein said body is composed of foam rubber.

4. An orthopedic device according to claim 2, wherein said body is composed of foam plastic.

* * * * *